(12) United States Patent
Carrez et al.

(10) Patent No.: US 8,251,923 B2
(45) Date of Patent: Aug. 28, 2012

(54) DEVICE FOR INTRODUCING A CATHETER GUIDE WIRE INTO A VESSEL

(75) Inventors: Jean-Luc Carrez, Ecouen (FR); Valery Dalle, Croix (FR); Pierrick Guyomarc'h, Ermont (FR)

(73) Assignee: Vygon, Ecouen (FR)

(*) Notice: Subject to any disclaimer, the term of this patent is extended or adjusted under 35 U.S.C. 154(b) by 104 days.

(21) Appl. No.: 12/666,921

(22) PCT Filed: Jul. 2, 2008

(86) PCT No.: PCT/EP2008/058515
§ 371 (c)(1),
(2), (4) Date: Dec. 28, 2009

(87) PCT Pub. No.: WO2009/004031
PCT Pub. Date: Jan. 8, 2009

(65) Prior Publication Data
US 2010/0179484 A1    Jul. 15, 2010

(30) Foreign Application Priority Data

Jul. 2, 2007    (FR) .................................... 07 56222

(51) Int. Cl.
*A61B 5/00*    (2006.01)
*A61M 25/00*    (2006.01)
*A61M 25/16*    (2006.01)

(52) U.S. Cl. ........................ 600/585; 604/533
(58) Field of Classification Search .................. 600/585; 604/167.04, 171, 256, 509, 200, 202, 205, 604/206, 237, 241, 244, 537, 96.01, 533; 128/912, 917; 206/403, 409, 438; 222/525; 251/149

See application file for complete search history.

(56) References Cited

U.S. PATENT DOCUMENTS

| | | | |
|---|---|---|---|
| 5,125,905 A | 6/1992 | Wright et al. | |
| 5,279,573 A * | 1/1994 | Klosterman | ................ 604/171 |
| 5,336,192 A * | 8/1994 | Palestrant | ............... 604/167.04 |
| 2004/0122416 A1 | 6/2004 | Schweikert | |
| 2005/0148997 A1* | 7/2005 | Valley et al. | ................ 604/509 |
| 2005/0177043 A1 | 8/2005 | Windheuser | |
| 2008/0108956 A1* | 5/2008 | Lynn et al. | ................ 604/256 |

FOREIGN PATENT DOCUMENTS

WO    9912600 A1    3/1999

* cited by examiner

*Primary Examiner* — Brian Szmal
(74) *Attorney, Agent, or Firm* — Levine & Mandelbaum

(57) ABSTRACT

A device for introducing a catheter guide wire into a vessel of a patient has a connector and a straightener for a J-shaped end of the guide wire, the connector having an axial bore, and its distal end and proximal end permitting a connection of the Luer type to a needle and to a syringe, respectively. The connector supports, on its inside, a sealing valve equipped with a slit, and the axial bore has, in its portion between the sealing valve and the distal end of the connector, a leaktight mating surface, the shape of which is such that it permits liquid-tight mating with the outer surface of the distal end of the straightener, when the latter is introduced into the connector via the sealing valve.

7 Claims, 3 Drawing Sheets

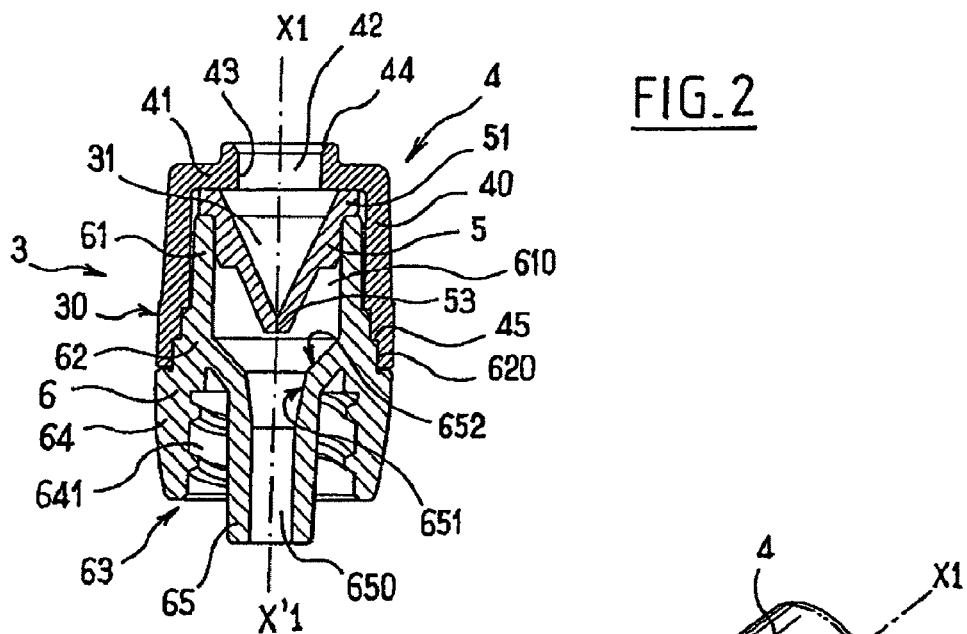
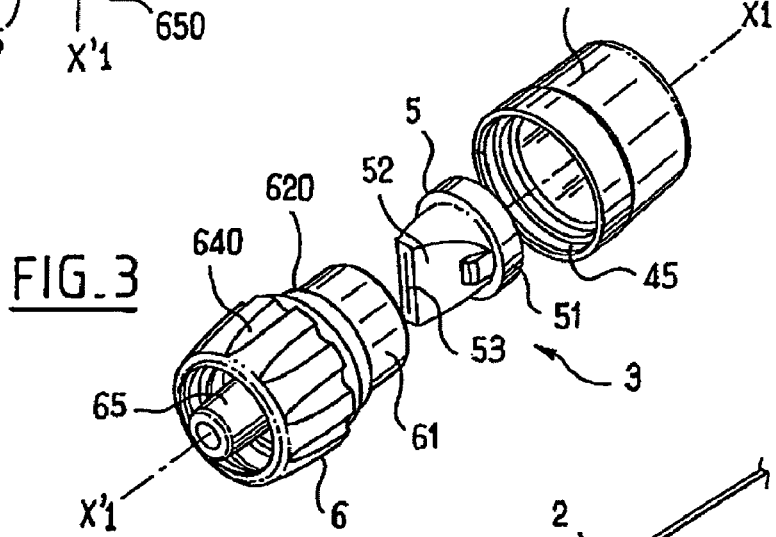
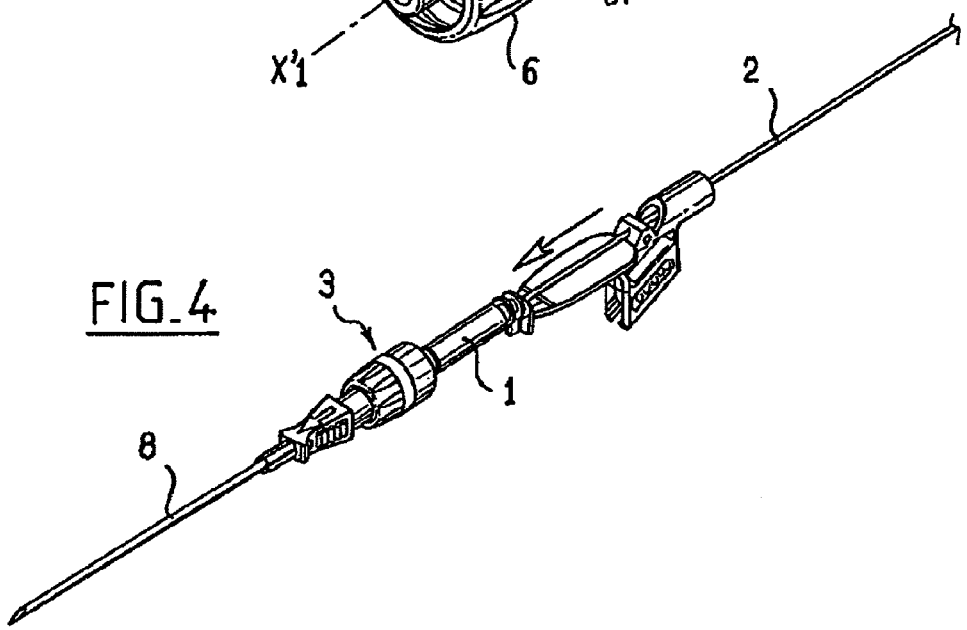

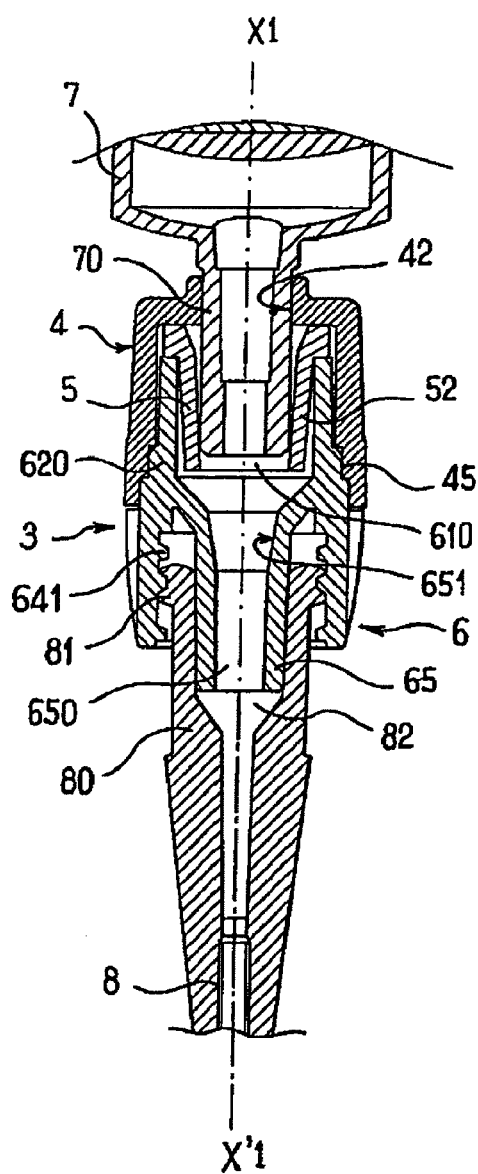
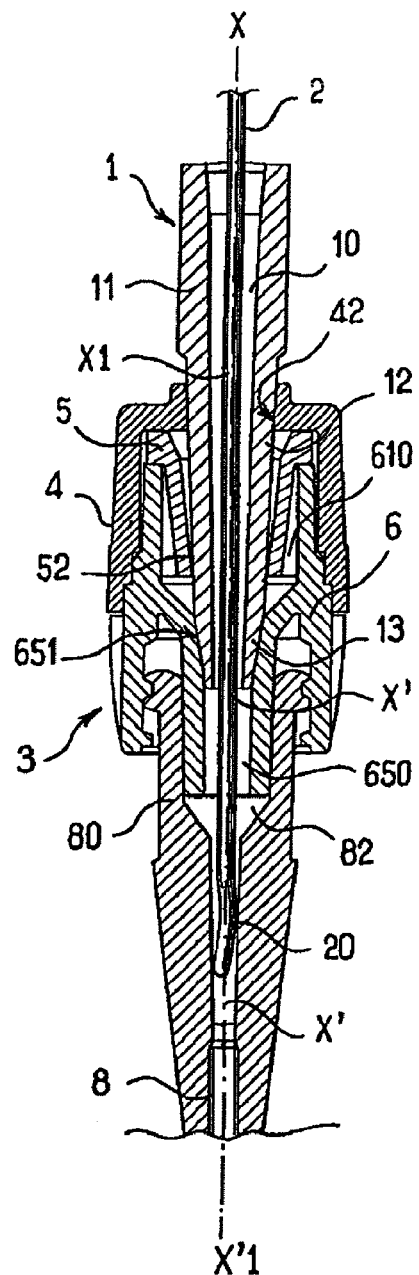

DEVICE FOR INTRODUCING A CATHETER GUIDE WIRE INTO A VESSEL

BACKGROUND OF THE INVENTION

The invention is located in the field of medical instrumentation; more specifically catheters intended to be introduced into the blood of lymph stream of patients.

The present invention relates to a device for introducing a flexible guide wire, with a J-shaped end, inside the circulatory system of a patient, this guide wire subsequently allowing placement of a catheter.

Central venous catheters may be introduced into the veins by sliding around a spiral and flexible guide, the latter having been introduced therein beforehand by means of a needle.

This technique is known to one skilled in the art under the name of the "Seldinger technique". It will now be briefly described with reference to the enclosed FIGS. 1A-1F I which are diagrams illustrating the main steps.

Referring to FIG. 1A, it may be seen that when a practitioner wants to insert a catheter into a vein, the walls of which are rather thin, to do this he/she uses a flexible spiral guide G, the distal end E of which has a shape curved on itself, said to be "J-shaped". The specific shape of this distal end E enables it to be introduced into the inside of the vein, without either damaging the walls of the latter or piercing them.

However, it is necessary to straighten out the J-shaped distal end of this guide wire before introducing it into the vein. For this purpose, the practitioner uses a straightener R with a conical shape, provided with an axial lumen of small diameter. He/she introduces the guide wire G through the distal end E of the straightener R and exerts traction on the latter (arrow H), until the distal end E of this wire is straightened. It is then found in the situation illustrated in FIG. 1B.

Next, as this may be seen in FIG. 1C, the practitioner uses a syringe S provided with an aspiration needle A in order to pass through the skin P of the patient. Once the bevel of the needle A is in the flesh and under the skin, he/she pulls on the piston of the syringe (arrow I), thereby creating a vacuum in the latter and in the needle. The practitioner then pushes on the needle and when the bevel of the latter penetrates into the vein V, blood is sucked up inside the syringe S, so that he/she may visually ascertain that the bevel of the needle is properly positioned in the vein V.

The practitioner then removes the syringe S from the base of the needle A, this situation being illustrated in FIG. 1D. Next, he/she introduces into the interior of the base of the needle, the distal end of the straightener R, inside which the guide wire G is found in the straightened position.

The practitioner then pushes the guide wire G through the straightener R and the needle A, as far as into the vein v (arrow J). This situation is illustrated in FIG. 1E.

The small distance between the distal end of the straightener R and the proximal end of the base of the needle A does not allow the J-shaped end of the guide wire to bend, so that the latter is forced to move forward along a straight line as far as into the vein V.

Finally, the practitioner removes the straightener R and the needle A by sliding them along the guide wire G and he/she then engages the tube of the catheter C on the guide wire G (arrow K), until the catheter is engaged over a certain distance in the vein V, as illustrated in FIG. 1F. He/she is assisted for this by marks present on the tube of the catheter which allow it to be located.

This technique however has drawbacks in that it requires many manipulations and in that blood losses may be significant, notably when the syringe S is disconnected from the needle A, as this is illustrated in FIG. 1D.

Moreover, when it is desired to insert a catheter inside an artery, it will be noted that the guide wire G does no longer necessarily have a J-shaped end, since the walls of the arteries are more resistant and harder, the risk of piercing them is lesser.

The technique for introducing the catheter is the same as the one which was just described for a vein, except that it is no longer necessary to use a syringe for viewing blood backflow, and therefore the proper position of the bevel of the needle in the artery. However, taking into account the pressure prevailing inside arteries, blood losses may be much more significant before complete introduction of the guide wire G inside the artery.

In order to improve the Seldinger technique described earlier and also to limit blood losses, several devices have been developed. Two of them are described in documents WO 90/11098 and WO 99/12600.

These devices respectively consist in a syringe, the piston of which has been modified in order to allow introduction of a catheter without blood losses, and in a syringe provided with a switch.

However, these devices are complex, which make them more expensive to manufacture and more complicated to use. Indeed, upon using one of these two systems, the practitioner is found pricking with bulky equipment: the needle plus the syringe plus the guide straightener plus the wound guide in a protective tube. On the other hand, the guides are often long (twice the length of the catheter), and, in order to avoid that they hang about on the field before introduction (=lack of asepsis) they are in a long and bulky protective tube.

A connector capable of being mounted on an aspiration needle or between this needle and a syringe is also known from document U.S. Pat. No. 5,336,192, for introducing an angiography catheter inside a lymph or blood vessel.

This connector interiorly includes a slit elastomeric disk. When the connector is connected to a syringe, the cone of the latter moves the walls of the disk apart, which allows communication between the syringe and the needle for vacuum and aspiration operations. After disconnecting the syringe, the disk closes back while preventing any loss of blood.

This document also describes the possibility of using a guide wire straightener and introducing the latter in the connector upstream from the elastomeric disk, and then of pushing the guide wire through the slit of this disk as far as into the vein.

However, such a device has the drawback of not being perfectly sealed, since it is difficult to guarantee the perfect seal of a slit around a guide wire of cylindrical shape.

The object of the invention is to find a remedy to these drawbacks.

SUMMARY OF THE INVENTION

For this purpose, the invention relates to a device for introducing a wire with a J-shaped end, into a blood or lymph vessel of a patient, this wire being used for guiding a catheter, this device comprising a connector and a straightener of the J-shaped end of said guide wire, said connector comprising a body crossed by an axial bore which extends between both of its opposite so-called "distal" and "proximal" ends, said distal and proximal ends allowing a connection of the Luer type with the base of a needle and with the distal end of a syringe, respectively.

According to the invention, said connector supports inside a sealing valve provided with a slit cutting the axis of said axial bore, and said axial bore comprises in its portion located between said sealing valve and the distal end of the connector, a surface, a so-called "leaktight mating" surface, the shape of which is such that it allows liquid-tight mating with the outer surface of the distal end of said straightener, when the latter is introduced into said connector through said sealing valve.

According to other advantageous and nonlimiting features of the invention, either taken alone or as a combination:

said leaktight mating surface is of frustoconical shape, its conicity decreasing towards the distal end of the connector;

the distal end of said connector is of a tubular shape and its length is such that it may be driven into the inside of the base of a needle, sufficiently deeply so that the J-shaped end of said guide wire cannot bend on itself, when this wire is inserted into the needle through said connector;

the proximal end of said connector is an orifice, the diameter of which is adapted to the outer diameter of a portion of the outer surface of said straightener, so as to guarantee a liquid-tight connection with the latter when said straightener is introduced into said connector through the sealing valve;

said connector is in two so-called "cap" and "lock" portions respectively, said cap including the proximal end of the connector and the lock its distal end, the cap and the lock being provided with mating assembling means and maintaining said sealing valve when they are assembled;

said sealing valve has the shape of a duckbill;

said straightener is pierced with an axial lumen, the diameter of which is sufficiently large for letting through the guide wire when its J-shaped end is deployed and sufficiently small for avoiding that this J-shaped end bends on itself and the outer surface of the distal end of the straightener has a shape and suitable dimensions for ensuring liquid-tight mating with said leaktight mating surface of the connector.

Other features and advantages of the invention will become apparent from the description which now will be made, with reference to the appended drawings, which illustrate as an indication, but not as a limitation, a possible embodiment.

DESCRIPTION OF THE DRAWINGS

In these drawings:

FIGS. 2 and 3 are longitudinal sectional and exploded perspective views respectively of the connector portion of the device according to the invention, FIG. 3 being at a smaller scale than that of FIG. 2, FIG. 4 is a perspective view of the device according to the invention mounted on a needle, FIG. 5 is an axial longitudinal sectional view of the connector, the latter being mounted between the end of a syringe and the base of a needle, and FIG. 6 is an axial longitudinal sectional view of this same connector, the syringe having been replaced with the straightener of the guide wire.

DESCRIPTION OF THE PREFERRED EMBODIMENT

Figure 1A:
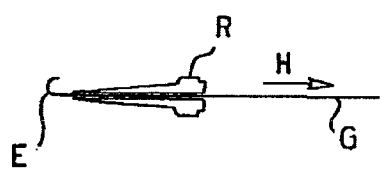
FIGS. 1A-1F are diagrams illustrating the different successive phases for introducing a guide wire, and then a catheter, into the interior of a vessel of a patient, according to the so-called "Seldinger" technique.
Figure 1B:
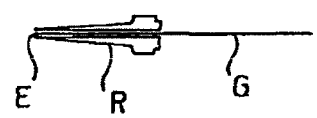
Figure 1C:
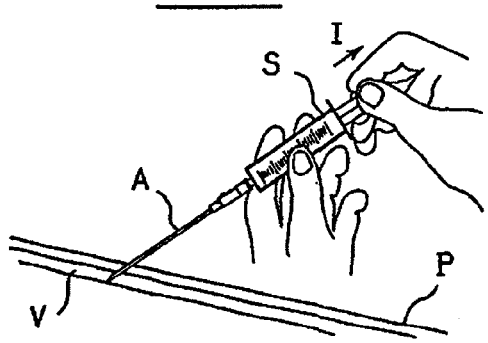

The device according to the invention is a pair consisting of a straightener 1 and a connector 3.

Referring to FIG. 6, it may be seen that the straightener 1 has a general elongated and tubular shape.

It is crossed right through by a lumen 10 which extends along its longitudinal axis X-X'.

The straightener includes three portions, i.e. a proximal end 11 with a larger diameter allowing it to be gripped by the practitioner, a conical distal opposite end 13 and a middle portion 12, the conicity of which is of a smaller slope than that of the distal end 13 and which extends between said ends 10 and 13.

The lumen 10 is also of a slightly conical shape, its diameter decreasing between the proximal end 11 and the distal end 13, in order to facilitate the introduction of a guide wire 2, such a wire being currently available commercially.

This guide wire 2 is a wire of flexible material, one of the ends 20 of which is in the natural condition bent on itself, whence its name of J-shaped end.

This guide wire 2 inside the straightener 1 and its positioning so as to straighten out the J-shaped end 20 thereof before introducing it into a vessel are identical with what has been described earlier in the introduction of the present application.

Referring to FIG. 2, it may be seen that the connector 3 comprises a body 30 with a general cylindrical tubular shape, crossed by an axial bore 31 which extends along a longitudinal axis X1-X'1.

The connector 3 is preferably made in two portions, i.e. a cap 4 and a lock 6, which clasp a sealing valve 5.

These various elements will now be described in more detail.

The cap 4 has the shape of a tubular sleeve with a longitudinal axis X1-X'1, of which one of the ends is folded, so as to define an annular flange 41 which extends radially towards the interior of the sleeve 40.

This flange 41 thus delimits an orifice 42, the diameter of which is smaller than that of the sleeve 40 of the connector.

This orifice 42 extends over a small height. Its circular inner wall bears numerical reference 43.

This orifice 42 has at its opening a conical flare or countersink 44 which guides and facilitates the introduction of a syringe or of the straightener, as this will be described later on.

At its opposite end, the cap 4 has on its inner face mating means 45 for coupling with the lock 6. These means are for example a threading or an ultrasonic weld, or an adhesive bond, or a fit with clips.

The orifice 42 defines the female proximal end of the connector 3 and allows a Luer type connection with a standard syringe or the aforementioned straightener.

The lock 6 has a general tubular shape with a longitudinal axis X1-X'1. It includes a cylindrical proximal end 61, the outer diameter of which is very slightly smaller than the inner diameter of the sleeve 40, so that it may engage into the latter.

The lock 6 continues with a middle area 62, the outer surface of which bears coupling means 620, complementary to the means 45.

Finally, the distal end 64 of the lock 6 comprises two coaxial tubes 64 and 65, with an axis X1-X'1.

The outer tube 64 includes a notched outer surface 640 which defines a knurl facilitating gripping and handling of the lock 6.

The tube 64 further has a female interior threading 641 which allows leaktight screwing of the base of a needle of the type of those currently found commercially, notably an aspiration needle.

The inner tube 65 or "cylinder" is an integral part of the remainder of the lock 6. It comprises a central bore 650, the upper portion of which is flared as a double frustum bearing numerical references 651 and 652. The portion 652 of the bore, more flared than the portion 651, connects to the bore 610 of larger diameter, made inside the tubular end 61.

The slope of the frusto-conical portion 651 of the bore is designed so as to correspond to that of the conical distal end 13 of the straightener 1 and to guarantee liquid-tight mating with the latter, when the straightener 1 is introduced into the connector (see FIG. 6). This portion 651 may also have another shape from the moment that it guarantees the seal.

By referring to FIG. 5, it may be seen that the outer diameter of the cylinder 65 is very slightly smaller than the inner diameter of the bore 82 made in the base 80 of the needle 8, so as to be introduced into the latter. The proximal end of the base 80 on its outer face is provided with a male threading 81 capable of cooperating with the inner female threading 641 of the tube 64.

The complementarity of the threads 81 and 441 on the one hand and the shape complementarity of the cylinder 65 and of the bore 82 on the other hand allow the needle 8 to be attached on the connector 3, through a connection known to one skilled in the art under the name of "Luer lock".

Moreover, as this is better apparent in FIG. 6, it will be noted that the dimensions, the shape and the length of the cylinder 65 of the connector are such that it penetrates as far as the bottom of the bore 82 of the base of the needle 8, so that the J-shaped end 20 of the guide wire 2 cannot bend on itself, when it penetrates into the base 80 of the needle 8.

The cap 4 and the lock 6 are advantageously made in plastic material for example: ABS (acrylonitrile-butadiene-styrene), polypropylene, POM (polyoxymethylene), polycarbonate, polyamide.

The valve 5 is preferably an anti-return valve, in the shape of a duckbill, made in a resilient plastic material, for example in elastomer, or further silicone, synthetic rubber such as polyisoprene, or elastomeric thermoplastics such as SEBS (styreneethylene-butylene-styrene).

As this is better apparent in FIG. 3, it comprises an annular proximal end 51 and a bevel-shaped distal end 52. This distal end is pierced with a slit 53 which cuts the axis X1-X'1.

As this may be seen in FIG. 2, when the cap and the lock 6 are assembled, they will clasp the proximal end 51 of the valve 5 between the flange 41 and the upper edge of the sleeve 61 so as to maintain the sealing valve 5 inside the connector.

The use of the connector 3 and of the straightener 1 according to the invention will now be described.

The practitioner introduces the distal end 70 or cone of the syringe 7 inside the proximal end 42 of the connector 3 so that this end 70 penetrates into the inside of the duckbill-shaped valve 5 and laterally pushes back the walls of the latter.

This position is illustrated in FIG. 5.

The resilient character of the elastomeric material making up said valve 5 tends to flatten the beveled walls 52 of the latter against the distal end 70 of the syringe 7.

Further, the orifice 42 cooperates with the distal end 70, so as to guarantee a sealed connection between both of these elements. The diameter of the orifice 42 is dimensioned accordingly.

The practitioner also screws in the base 80 of the needle 8 around the cylinder 65 of the connector.

As this may be seen in FIG. 5, with the short length of the entry 42 of the cap 4, the cone 70 of the syringe may enter over a significant length inside the connector, which then also allows significant opening of the duckbill-shaped valve 5.

The practitioner pushes in the syringe under the skin and pulls on the piston of the syringe, thereby creating vacuum in the latter and in the needle 8. This vacuum may be obtained by means of the seal existing between the orifice 42 of the cap 4 and the syringe.

Figure 1D:
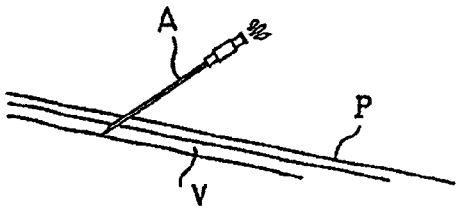
Figure 1E:
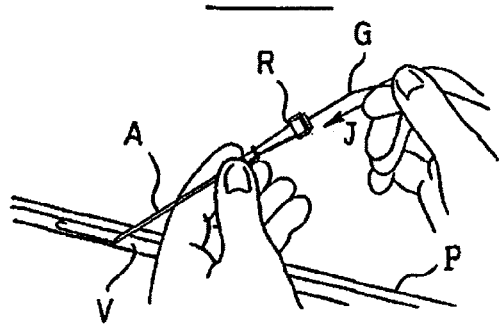

When the practitioner pushes the needle into the vein, and then removes the syringe, the valve 5 resumes its closed position illustrated in FIG. 2 and guarantees the liquid-tightness of the device. Blood cannot therefore escape out of the connector, as this was the case in the devices of the prior art (see FIG. 1D).

The practitioner then positions the guide wire 2 inside the straightener 1, so as to straighten out the J-shaped distal end 20; as explained earlier.

He/she then introduces the straightener 1 coaxially inside the connector 3, so that the straightener 1 pushes back the walls of the valve 5 outwards and is guided until its distal end 13 abuts against the frusto-conical inner face 651 of the lock 6, by creating at this level a leaktight connection.

This surface 651 therefore forms a "mating surface" which is liquid-tight.

Moreover, the leaktight connection is also ensured between the middle portion 12 of the straightener 1 and the walls of the proximal end 42 of the connector.

Unlike the device known from the state of the art, it is the straightener 1 which crosses the valve 5 and the liquid-tightness is ensured downstream at the surface 651. By no means, is the guide wire 2 in contact with the valve 5. A possible blood backflow is thereby prevented. Thus, the guide wire 2 is capable of freely sliding in a thereby formed tubular channel, and the practitioner does not have to fear any blocking of the guide wire which may lead to damage of the vein.

Moreover, blood may with difficulty pass between the guide wire 2 and the inner bull 10 of the straightener 1, and this, all the more so since the guide wire 2 is pushed in the distal direction. Moreover, blood present in the connector under the valve 5 cannot flow out through the inlet of the cap, since the straightener 1 sealably blocks the cavity 42. The pressure exerted by the beveled walls 52 of the valve 5 also contributes to guaranteeing the seal.

Figure 1F:
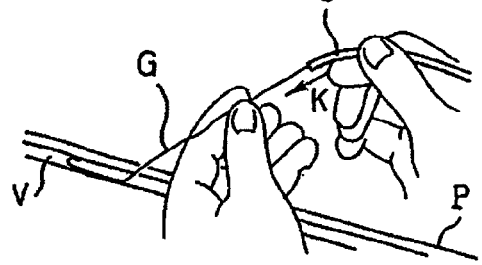

The practitioner pushes the guide wire 2 until the latter penetrates into the vein (see FIG. 4), and then removes the needle 8, connector 3 and straightener 1 assembly. He/she may then slide the catheter along the guide wire 2 as described earlier in connection with FIG. 1F.

The device according to the invention is simple to use and may avoid losses of blood such as those which may be observed with the devices of the prior art.

The invention claimed is:

1. A device for introducing a wire with a J-shaped end, into a blood or lymph vessel of a patient, said wire being used for guiding a catheter, wherein said device comprises a connector and a straightener of the J-shaped end of said guide wire, said connector comprising a body with an axial bore which extends between a distal end and a proximal end of said body, said distal end adapted for providing a Luer type connection with a base of a needle and said proximal end providing a Luer type connection with a distal end of a syringe, wherein said connector further comprises a sealing valve provided with a slit intersecting an axis of said axial bore and said axial bore has a portion between said sealing valve and the distal end of the connector adapted to receive a distal end of the straightener, wherein said portion has a mating surface in leaktight engagement with an outer surface of the distal end of said straightener, when said straightener is disposed within said sealing valve.

2. The device according to claim 1, wherein said mating surface has a frusto-conical shape with a diameter decreasing towards the distal end of the connector.

3. The device according to claim 1, wherein the distal end of said connector is of a tubular shape and has a length which prevents the J-shaped end of said guide wire from curving between said connector and said needle.

4. The device according to claim 1, wherein the proximal end of said connector is an orifice, the diameter of which is adapted to the outer diameter of a portion of the outer surface of said straightener, so as to form a liquid-tight connection between said connector and said straightener when said straightener is disposed within said sealing valve.

5. The device according to claim 1, wherein said connector comprises a cap and a lock, said cap including the proximal end of the connector and said lock including the distal end of the connector, the cap and the lock comprising complementary assembling means and maintaining said sealing valve when said cap and said lock are assembled.

6. The device according to claim 1, wherein said sealing valve has a duckbill shape.

7. The device according to claim 1, wherein said straightener comprises an axial lumen adapted to house the guide wire when the J-shaped end of said guide wire is deployed and capable of preventing said J-shaped end from curving.

* * * * *